US012624347B2

(12) United States Patent
Nag et al.

(10) Patent No.: US 12,624,347 B2
(45) Date of Patent: May 12, 2026

(54) WIRELESS ACTIVATION OF CHANNELRHODOPSIN VIA IN SITU SELF-ASSEMBLY OF SEMICONDUCTOR QUANTUM DOTS AT THE PLASMA MEMBRANE

(71) Applicant: The Government of the United States of America, as represented by the Secretary of the Navy, Arlington, VA (US)

(72) Inventors: Okhil K. Nag, Brandywine, MD (US); Megan E. Muroski, Milwaukee, WI (US); Michael H. Stewart, Springfield, VA (US); Alexander Efros, Annandale, VA (US); Scott Walper, Springfield, VA (US); James Delehanty, Washington, DC (US); Eunkeu Oh, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 699 days.

(21) Appl. No.: 17/932,995

(22) Filed: Sep. 16, 2022

(65) Prior Publication Data

US 2023/0091507 A1    Mar. 23, 2023

Related U.S. Application Data

(60) Provisional application No. 63/246,111, filed on Sep. 20, 2021.

(51) Int. Cl.
*C12N 13/00*    (2006.01)
*C07K 14/405*    (2006.01)

(52) U.S. Cl.
CPC ............ *C12N 13/00* (2013.01); *C07K 14/405* (2013.01)

(58) Field of Classification Search
CPC .... C12N 13/00; C12N 5/0006; C12N 5/0619; C12N 5/062; C12N 5/0657; C12N 5/0658; C12N 5/0661; A61N 5/062; A61N 2005/0662; A61N 47/6929; A61N 5/06; A61N 5/067
See application file for complete search history.

(56) References Cited

U.S. PATENT DOCUMENTS

| | | | |
|---|---|---|---|
| 10,705,092 B2 | 7/2020 | Delehanty | |
| 10,780,185 B2 | 9/2020 | Delehanty | |
| 2007/0054319 A1* | 3/2007 | Boyden | A61P 29/00 435/7.1 |
| 2014/0056815 A1* | 2/2014 | Peyman | A61K 49/085 424/9.4 |

OTHER PUBLICATIONS

Nag, OK et al. In situ self-assembly of quantum dots at the plasma membrane mediates energy transfer-based activation of channelrhodopsin. Particle & Particle Systems Characterization. 2021. 38: 2100053. 7 pages. Published online Jun. 19, 2021. (Year: 2021).*
Papagiakoumou, E et al. Scanless two-photon excitation of channelrhodopsin-2. Nature Methods. 2010. 7(10): 848-854. (Year: 2010).*
Hososhima, S et al. Near-infrared (NIR) up-conversion optogenetics. Scientific Reports. 2015. 5:16533. 9 pages. (Year: 2015).*
Proft, J et al. From opto- to radio-genetics: A switch in the wavelength. Communicative & Integrative Biology. 2012. 5(3): 227-229. (Year: 2012).*
Dif, A et al. Small and stable peptidic PEGylated quantum dots to target polyhistidine-tagged proteins with controlled stoichiometry. JACS. 2009. 131: 14738-14746. (Year: 2009).*
Bouchonville, N.; Le Cigne, A.; Sukhanova, A.; Saab, M.-b.; Troyon, M.; Molinari, M.; Nabiev, I., Controlled FRET efficiency in nano-bio hybrid materials made from semiconductor quantum dots and bacteriorhodopsin. Pro. SPIE 2012, 8460.
Carvalho-de-Souza, João L.; Treger, Jeremy S.; Dang, B.; Kent, Stephen B. H.; Pepperberg, David R.; Bezanilla, F., Photosensitivity of Neurons Enabled by Cell-Targeted Gold Nanoparticles. Neuron 2015, 86, 207-217.
Carvalho-de-Souza, João L.; Nag, Okhil. K; Oh, Eunkeu; Huston, Alan L.; Vurgaftman, Igor; Pepperberg, David R.; Bezanilla, Francisco; Delehanty, James B., Cholsterol Functionalization of Gold Nanoparticles Enhances Photoactivation of Neural Activity. ACS Chem Neurosci., Mar. 20, 2019, 10(3), 1478-1487.
Griep, M. H.; Walczak, K. A.; Winder, E. M.; Lueking, D. R.; Friedrich, C. R., Quantum Dot Enhancement of Bacteriorhodopsin-Based Electrodes. Biosens. and Bioelectron. 2010, 25, 1493-1497.
Griep, M. H.; Winder, E. M.; Lueking, D. R.; Garrett, G. A.; Karna, S. P.; Friedrich, C. R.; Förster Resonance Energy Transfer between Core/Shell Quantum Dots and Bacteriorhodopsin. Mol. Biol. Int. 2012, 2012, Article ID 910707.

* cited by examiner

*Primary Examiner* — David W Berke-Schlessel
*Assistant Examiner* — Susan E. Fernandez
(74) *Attorney, Agent, or Firm* — US Naval Research Laboratory; Fariborz Moazzam

(57) ABSTRACT
A quantum dot (QD)-rhodopsin bioconjugate system uses Förster resonance energy transfer (FRET)-mediated induction of cellular membrane depolarization via optical activation of ion channel proteins channelrhodopsin (ChR).

6 Claims, 7 Drawing Sheets
(7 of 7 Drawing Sheet(s) Filed in Color)

Specification includes a Sequence Listing.

WIRELESS ACTIVATION OF CHANNELRHODOPSIN VIA IN SITU SELF-ASSEMBLY OF SEMICONDUCTOR QUANTUM DOTS AT THE PLASMA MEMBRANE

CROSS-REFERENCE TO RELATED APPLICATIONS

This application claims the benefit of U.S. Provisional Application No. 63/246,111 filed on Sep. 20, 2021, incorporated herein by reference in its entirety.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 114119.

INCORPORATION BY REFERENCE

This Application incorporates by reference the Sequence Listing XML file submitted via the patent office electronic filing system having the file name "114119-US2.XML" and created on Sep. 16, 2022 with a file size of 2,910 bytes.

STATEMENT REGARDING PRIOR DISCLOSURES BY THE INVENTOR(S)

A prior disclosure, Nag, O. K., Muroski, M. E., Field, L. D., Stewart, M. H., Oh, E., Susumu, K., Spangler, J. R., Walper, S. A., Delehanty, J. B., "In Situ Self-Assembly of Quantum Dots at the Plasma Membrane Mediates Energy Transfer-Based Activation of Channelrhodopsin," *Part. Part. Syst. Charact.* 2021, 2100053, was made by one or more of the inventors with other named authors. Those other authors who are not named as inventors of this patent application were working under the direction and supervision of at least one of the inventors.

BACKGROUND

The therapeutic modulation of membrane potential of electrically excitable cells has gained significant interest in recent years as membrane potential regulates proliferation, migration, and communication among neuronal cells and contraction in muscle cells. Furthermore, normal cells exhibit resting membrane potentials between −60 to −100 mV as compared to cancer cells, which have elevated resting membrane potentials between −55 mV to +5 mV. Exploiting the large differences in membrane potential provides a unique opportunity for researchers to target therapeutics specifically to cancer cells. However, at the single cell level, the functional control of ionic currents and ion channel activity using nanoscale devices has yet to be elucidated.

Optically activatable ion channel proteins in the cellular plasma membrane, such as channelrhodopsin (ChR), play critical rules in maintaining the membrane potential of excitable cells. ChRs are highly conserved seven transmembrane domain proteins containing an 11-cis-retinal chromophore that undergoes light-activated photoisomerization (typically with blue light) to open the channel and allow the passage of ions ($Na^+$, $K^+$, $Ca^{2+}$) into the cell. Recently, the development of genetically-encoded ChRs have opened up the possibility of light-activated control of membrane potential (optogenetics), but this requires cellular transfection with exogenous nucleic acids which poses challenges for their use in vivo. Further, genetically-encoded ChRs suffer from bleaching/inactivation, short lifetime in the activated state, and small two-photon absorption cross sections (~$10^2$ GM units) which limits their ability to be excited with longer wavelength light in the optical tissue transparency window (~700-1100 nm) where water and hemoglobin have minimal absorbance.

A need exists to overcome these limitations of ChRs.

BRIEF SUMMARY

In one embodiment, method of cell depolarization includes providing a cell expressing a channelrhodopsin protein comprising a polyhistidine domain on an extracellular portion thereof; contacting the cell with a quantum dot configured as a FRET donor to the channelrhodopsin and allowing the quantum dot to self-assemble via metal affinity coordination to the polyhistidine domain; and then stimulating the quantum dot to emit light, thereby optically activating the channelrhodopsin via a FRET process to depolarize the cell. In one aspect, the channelrhodopsin protein comprises SEQ ID NO: 1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a schematic of a 530 nm-emitting QD. The structure is a CdSe/ZnS core/shell QD capped with the zwitterioinic compact ligand, CL4. FIG. 2B shows absorbance (black trace) and fluorescence emission (green trace) spectra of the QD. The emission spectra was collected by exciting at 405 nm. FIG. 2C shows spectral overlap of the QD donor and ChR-C1V1 acceptor. Shown are the emission spectra of the QD (green trace) and the absorbance spectra of ChR-C1V1 (blue trace) displaying the significant spectral overlap between the QD emission and ChR absorbance.

FIG. 3A provides fluorescence images of (i) ChR-C1V1-iRFP682 (cyan), (ii) membrane-bound QDs (green), (iii) Rhodamine-DHPE membrane marker, and (iv) merged images showing colocalization of the QDs with ChR-C1V1-iRFP682. Scale bar, 10 µm. FIG. 3B contains confocal fluorescence images of cell monolayers expressing ChR-C1V1-iRFP682 and labeled with the potentiometric indicator dye DiSBAC$_2$(3). DiSBAC$_2$(3) response before photoactivation by 561 nm excitation (top) and after excitation (bottom). Areas of increased DiSBAC$_2$(3) signal are denoted by white arrow. FIG. 2C shows that cells expressing ChR-C1V1-iRFP682 show a significant depolarization response when excited with 561 nm laser (green) but no response when excited with 405 nm laser (blue)

FIG. 4A provides confocal fluorescence images of HEK 293T/17 cells expressing ChR-C1V1-iRFP682 (cyan) and labeled with DiSBAC2(3). The left column shows cells labeled with QDs before and after excitation with 405 nm laser. A significant increase in the DiSBAC2(3) signal is noted in multiple cells expressing ChR-C1V1-iRFP682 (white arrows). The right column shows the negligible DiSBAC2(3) response in cells not labeled with QDs and excited with 405 nm laser (yellow arrows). Scale bar 20 µm. FIG. 4B shows time-resolved Fluo-response of ChR-C1V1-iRFP682-expressing cells (+/–QDs) subjected to iterative excitation (1.9 µs/pixel) with 405 nm laser and images were captured in every 10 s over a 15 min time course.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is a technique to indirectly excite the retinal chromophore in ChRs via Förster resonance energy transfer (FRET) using optically active light-harvesting quantum dots (QDs) as energy donors. The QDs self-assemble to ChR via metal affinity coordination between the ZnS shell of the QD and a polyhistidine domain (e.g., a hexahistidine or His$_6$ tract) expressed on the extracellular domain of ChR. QD binding to the plasma membrane was found to be specific for the presence the His$_6$ domain on ChR as well as the ability to achieve a high degree of QD-ChR colocalization at the plasma membrane. ChR is activated by indirect excitation (via FRET) from the QD donor. In one embodiment, the QD is responsive to 405 nm light, such as from a laser, thus enabling two-photon excitation in the optical tissue transparency window (~700-1100 nm) where water and hemoglobin have minimal absorbance.

Figure 1:
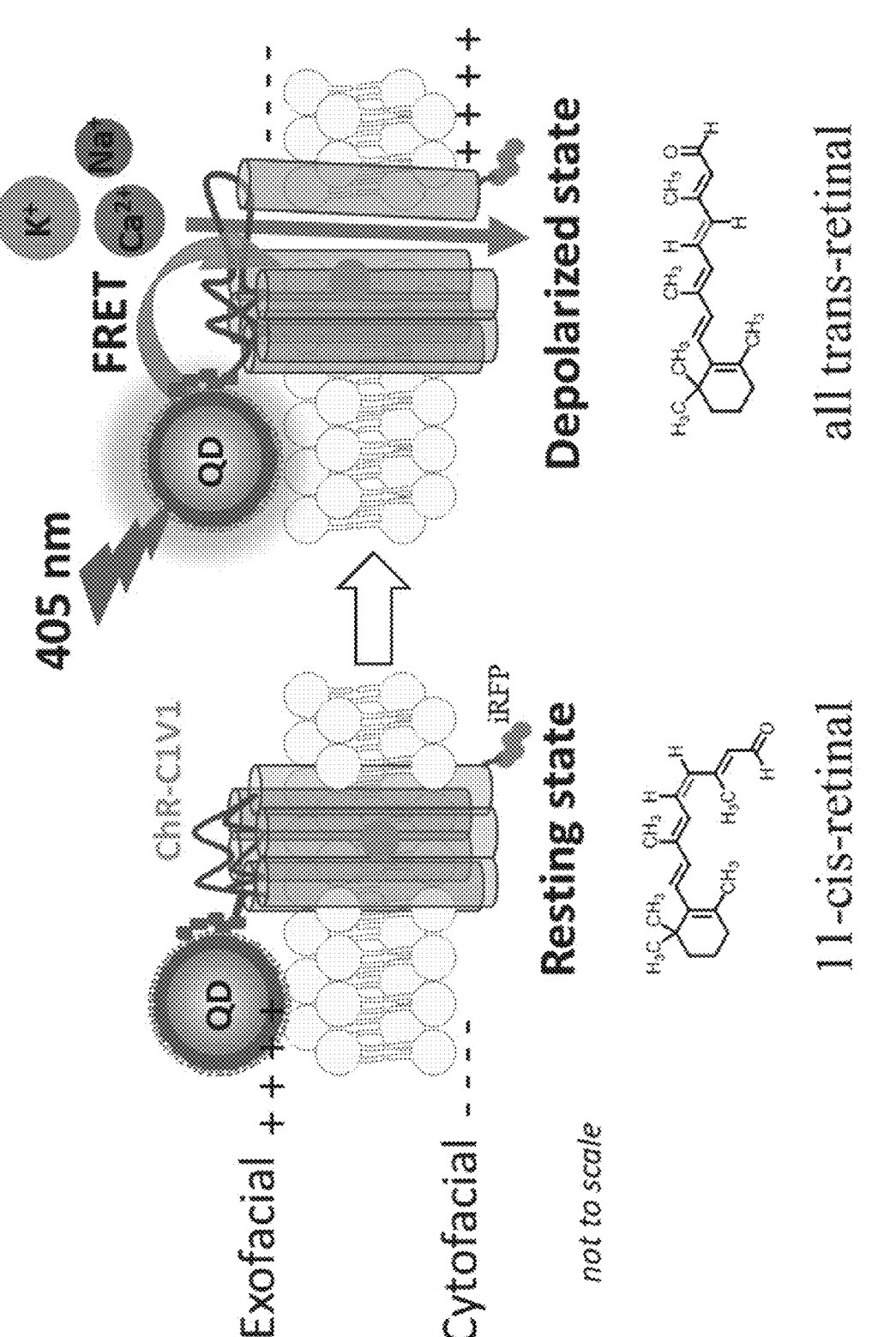
FIG. 1 schematically depicts the photoactivation of channelrhodopsin acceptor using a membrane-tethered quantum dot (QD) as a donor. A hydrophilic QD (as Förster resonance energy transfer donor) is self-assembled to the exofacial side of channelrhodopsin C1V1 ($His_6$-ChR-C1V1) via an N-terminal polyhistidine tract (red) that mediates metal affinity coordination to the ZnS shell of the QD. The QD donor self-assembles specifically to the ChR-C1V1 and is in close proximity to the 11-cis-retinal acceptor (orange dot). The QD acts as a light harvesting transducer to photoactivate the retinal moiety which undergoes photoisomerization, resulting in opening of the channel and the influx of $Na^+$, $K^+$, and $Ca^{2+}$ ions. Depolarization of membrane potential is iteratively controlled by excitation of the QD. In all experiments herein, $His_6$-ChR-C1V1 was expressed as a fusion with the red fluorescent protein, iRFP682 at its C-terminus for visualization

FIG. 1 schematically illustrates how QDs were designed to assemble in situ to ChR that was engineered to express an N-terminal His$_6$ tract. In this configuration, the QD FRET donor and the 11-cis-retinal acceptor located in ChR are brought in close proximity to each other to engage in efficient FRET.

Figures 2A, 2B, 2C:
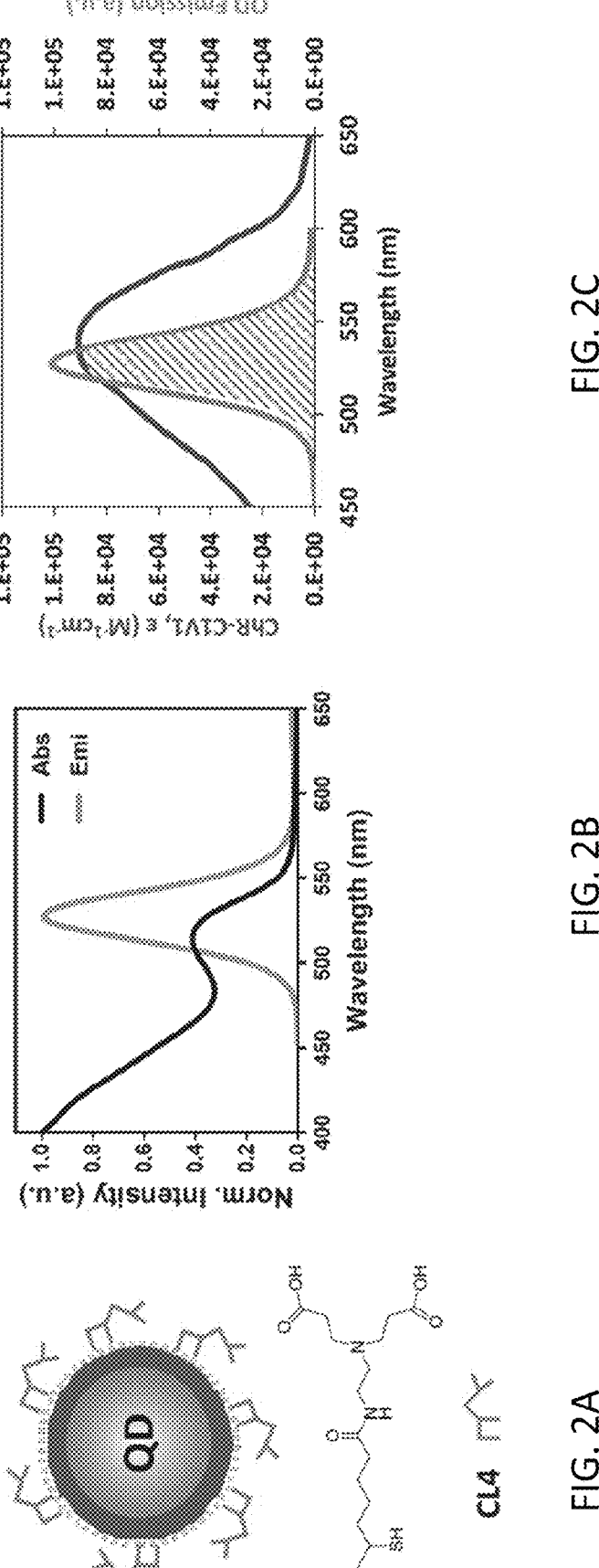
FIGS. 2A-2C illustrate photophysical properties of quantum dots (QDs) and channelrhodopsin (ChR).

One of the continuing challenges of interfacing QDs with ChR is controlling the optimal FRET distance between the QD donor and ChR acceptor on the plasma membrane. To this end, the colloidally stable CdSe/ZnS core/shell QDs can be synthesized with a short zwitterionic ligand (termed CL4) to enable close association of QD-ChR for efficient distance-dependent energy transfer. The molecular structure of the CL4 compact ligand is illustrated in FIG. 2A. The zwitterionic nature of CL4 renders the QDs colloidal stabile in aqueous environments and biocompatibile. The QDs self-assemble to ChR via metal affinity coordination interactions between the ZnS shell of the QD and a hexahistidine (His$_6$) tract expressed on the extracellular domain of ChR. The QD emission maximum (530 nm) (FIG. 2B) coupled with the absorbance maximum of the ChR (540 nm) facilitates significant spectral overlap that drives efficient FRET (FIG. 2C).

Examples

Figure 3A:
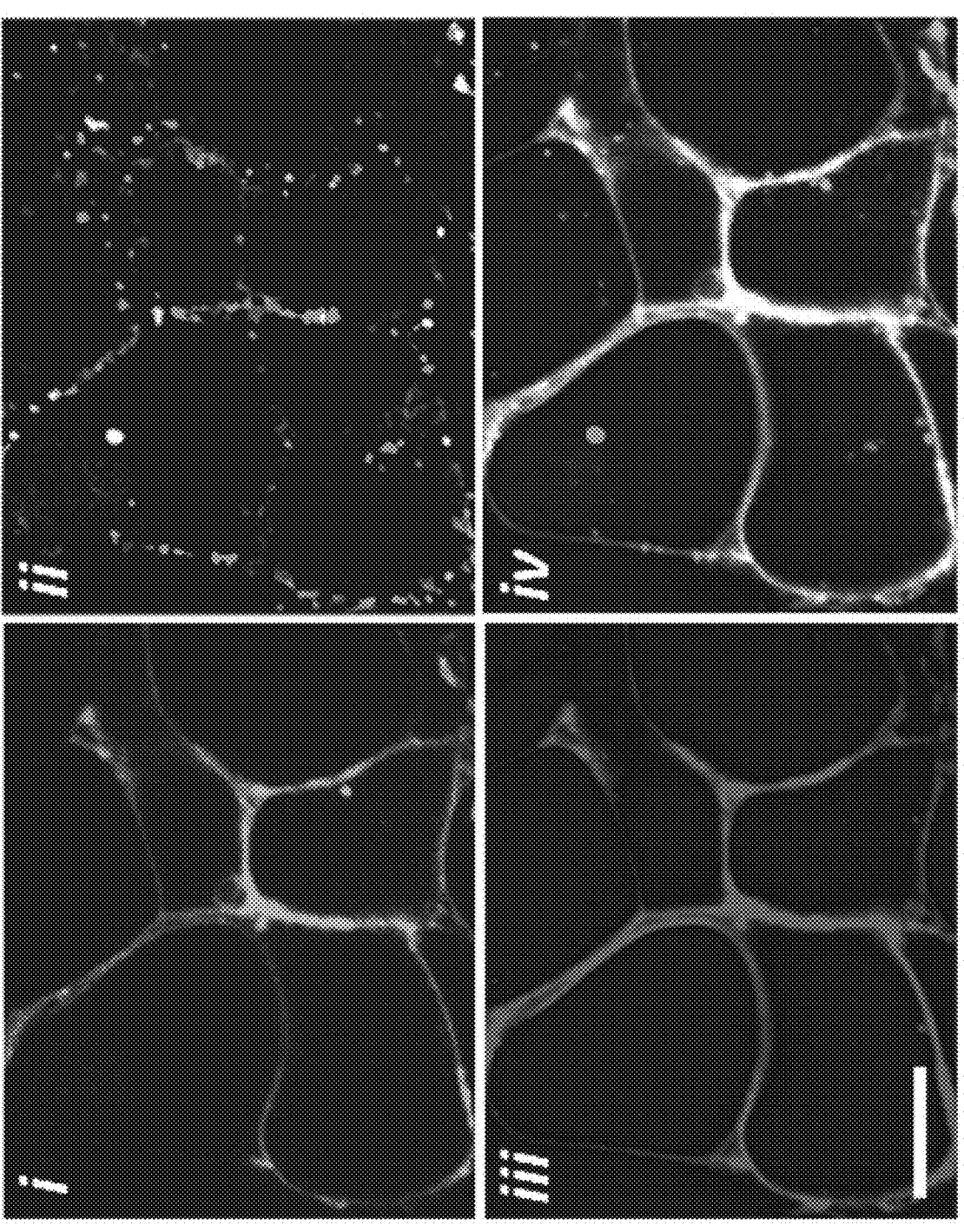
FIGS. 3A-3C show the expression and functionality of ChR C1V1-iRFP682 fusion protein. HEK 293T/17 cells were transfected with an expression vector encoding a construct termed ChR-C1V1-iRFP682 (SEQ ID NO: 1) that includes ChR-C1V1 with an N-terminal fusion to a hexahistidine tract and a C-terminal fusion to the red fluorescent protein, iRFP682.

The ChR-C1V1 channel was expressed as a fusion protein with a His$_6$ motif at its N-terminus (exofacial) and with the far red fluorescent protein, iRFP682 (excitation 640 nm/emission 682 nm) at its C-terminus using standard recombinant techniques. The His$_6$ motif enabled the facile self-assembly of water soluble QDs to the N-terminal end of the ChR-C1V1 while the iRFP682 enabled easy tracking of expression and localization of the protein. Henceforth, this construct is referred to as His$_6$-ChR-C1V1-iRFP, with SEQ ID NO: 1. Initial experiments confirmed the efficient expression and membrane localization of the His$_6$-ChR-C1V1-iRFP fusion protein. After 36 h post-transfection, HEK 293T/17 cells displayed a robust degree of membrane-localized expression of the protein where >50% of cells were positive for expression as evidenced by imaging iRFP fluorescence, as seen in FIG. 3A, subpart i. It was confirmed that the 530 nm QDs could self-assemble to the extracellularly-displayed His$_6$ domain on His$_6$-ChR-C1V1-iRFP. Clear and distinct labeling of the plasma membrane with the QDs occurred upon simple incubation with cell monolayers for ~20 min followed by washing (FIG. 3A, subpart ii). This was confirmed by the high degree of colocalization of the QD signal with both the His$_6$-ChR-C1V1-iRFP signal and with the plasma membrane marker, Lissamine™ Rhodamine B 1,2-dihexadecanoyl-sn-glycero-3-phosphoethanolamine (DHPE-Rhod, FIG. 3A, subpart iv). Using Pearson's colocalization analysis it was determined that there was 96% and 87% overlap, respectively, of the His$_6$-ChR-C1V1-iRFP and QD signal with the DHPE-Rhod membrane marker, confirming the highly efficient localization of the ChR and QDs at the plasma membrane. Additionally, the degree of overlap of the QD signal with the His$_6$-ChR-C1V1-iRFP signal was ~85%, which gave a strong indication that the QD and ChR protein could be in close enough proximity to each to engage in FRET. The QDs remained resident on the membrane for the duration of the experimental window (~2 h). It was also evident that the binding of the QDs to the plasma membrane was specific for the presence of the His$_6$ tract on His$_6$-ChR-C1V1-iRFP as cells that were not transfected with the fusion protein showed negligible QD fluorescence signal after incubation.

Figure 3B:
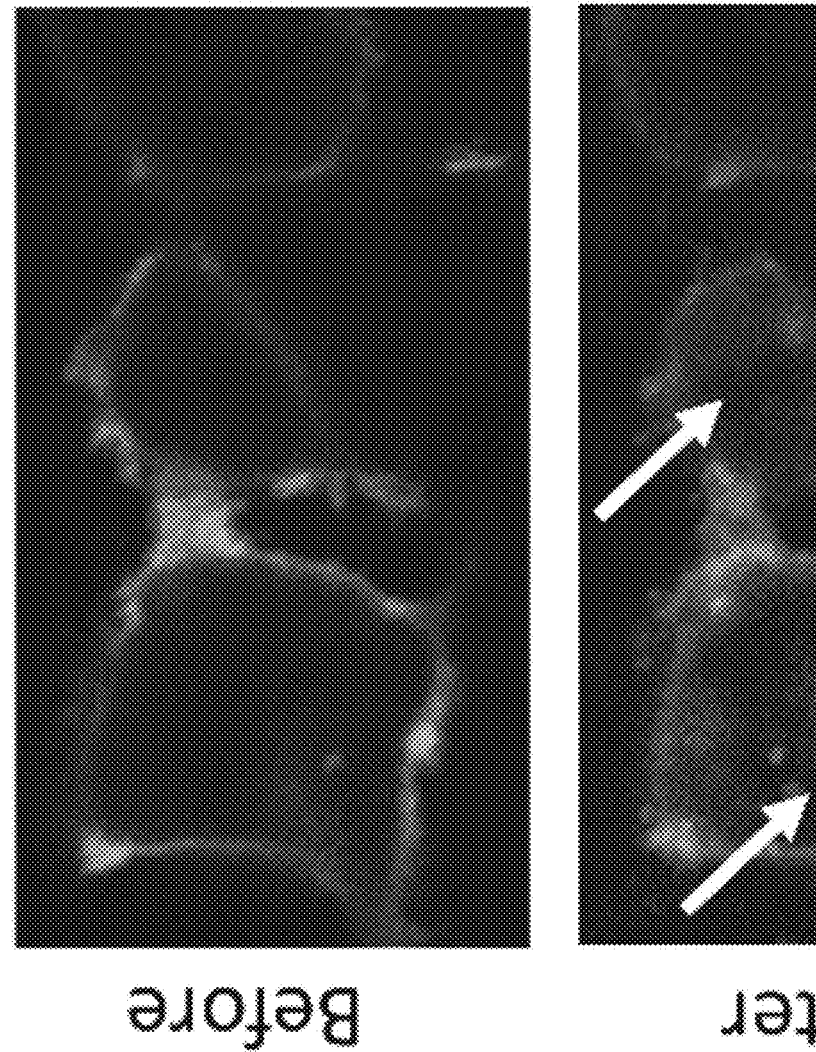
Figure 3C:
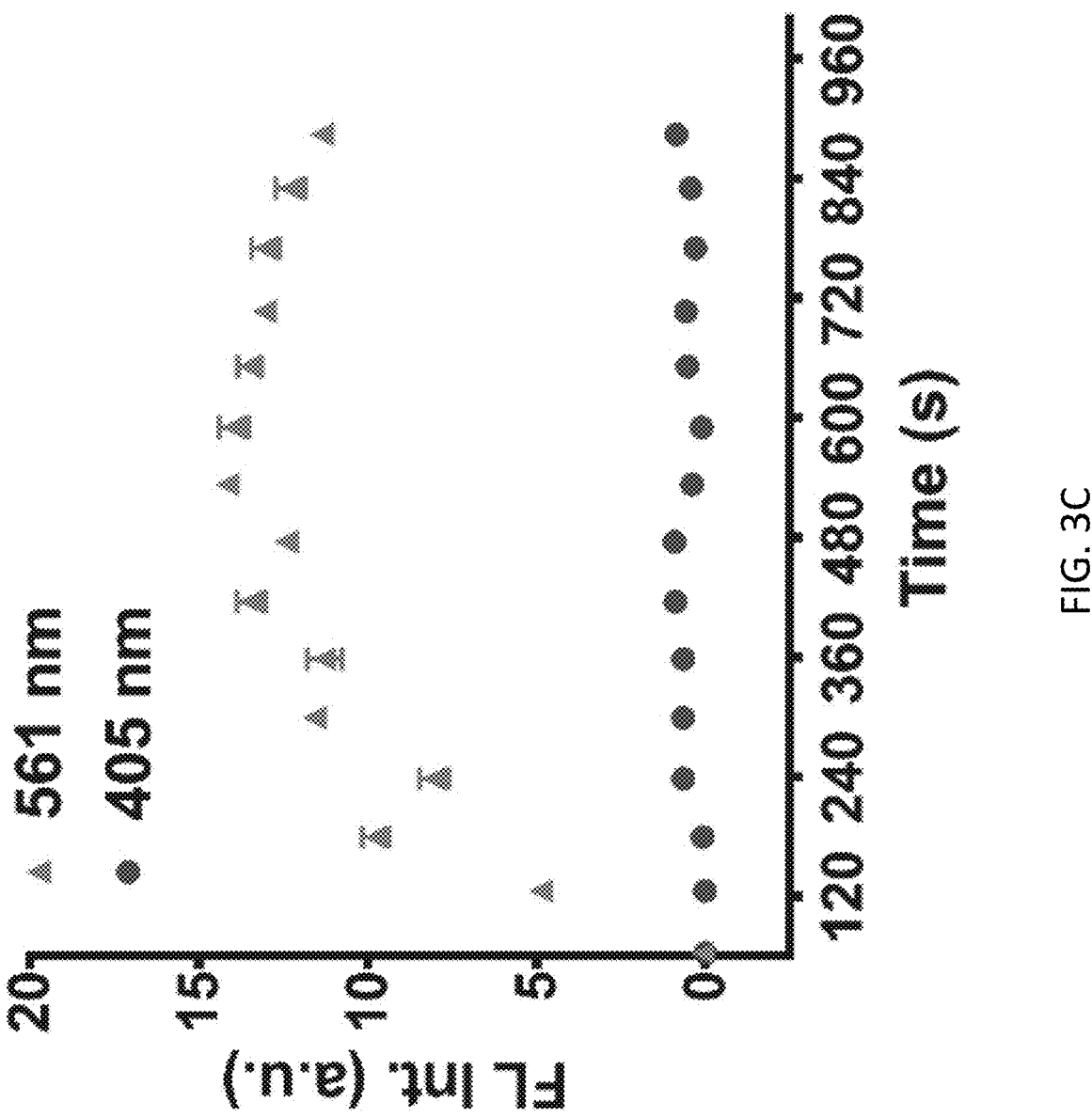

The functionality of the His$_6$-ChR-C1V-iRFP was confirmed by assessing the ability of the ion channel protein to be activated when stimulated with the 561 nm laser. As shown in the fluorescence micrographs in FIG. 3B, cells expressing His$_6$-ChR-C1V1-iRFP and also co-labeled with the potentiometric indicator dye, DiSBAC$_2$(3), showed a significant increase in plasma membrane depolarization upon laser excitation. These results are represented graphically in FIG. 3C where time-resolved data collected from HEK 293T/17 cells showed several important features of the system. First, the cells showed an increasing DiSBAC2(3) response that increased steadily over a 9 min time period as the His$_6$-ChR-C1V1-iRFP was iteratively activated with the 561 nm laser every 60 sec. Second, fusion to the iRFP did not affect the activity of the channel protein. Finally, and most importantly, the His$_6$-ChR-C1V1-iRFP ion channel was not activated by the 405 nm laser as there was no measurable fluorescence signal above background observed for the DiSBAC$_2$(3) probe when cells were excited at this wavelength. This observation firmly established that any observed activation of the His$_6$-ChR-C1V1-iRFP ion channel with the 405 nm laser would be driven specifically by energy transfer from the light-harvesting QD.

Figure 4A:
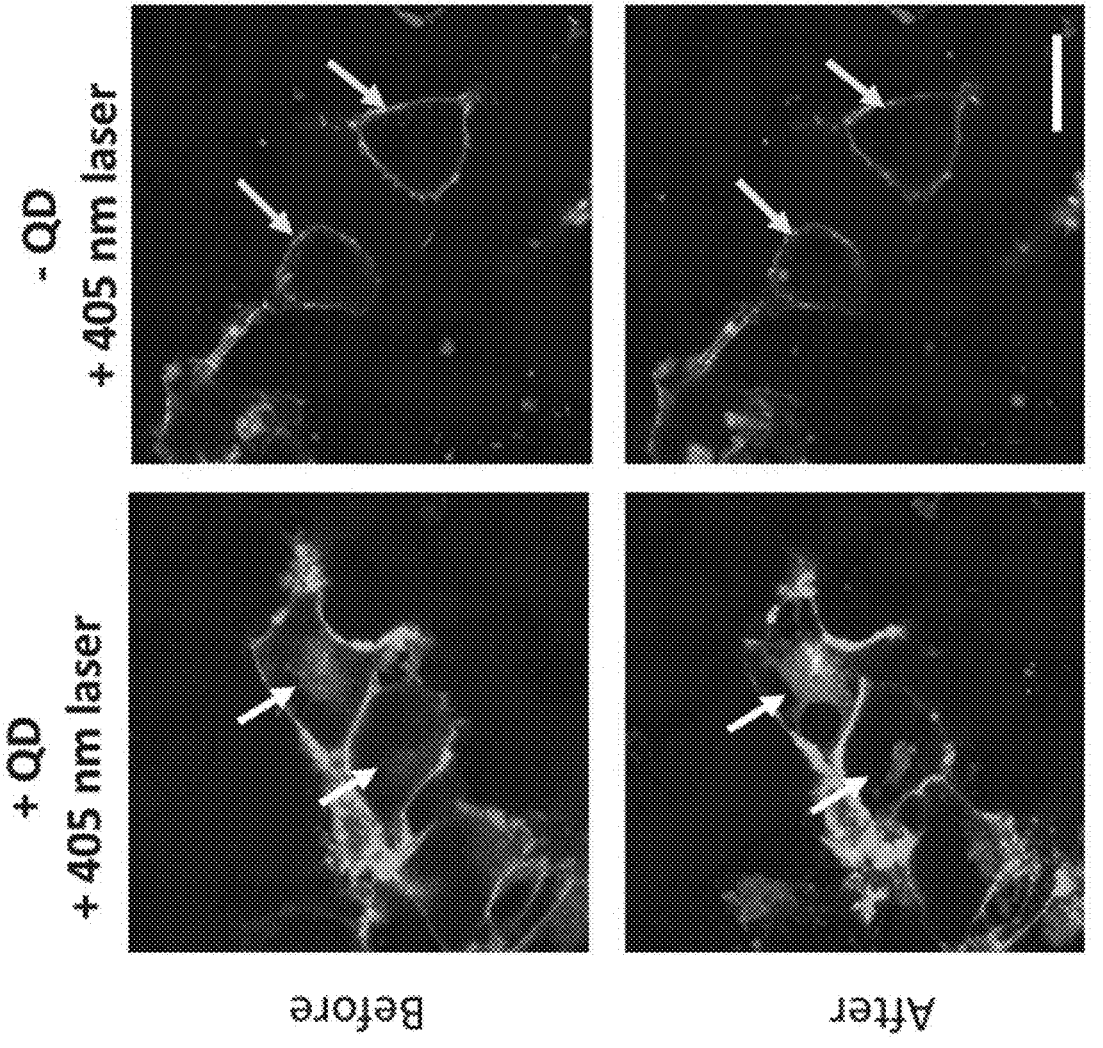
FIGS. 4A and 4B show QD-mediated photoinduction of depolarization in HEK 293T/17 cells expressing ChR-C1V1.
Figure 4B:
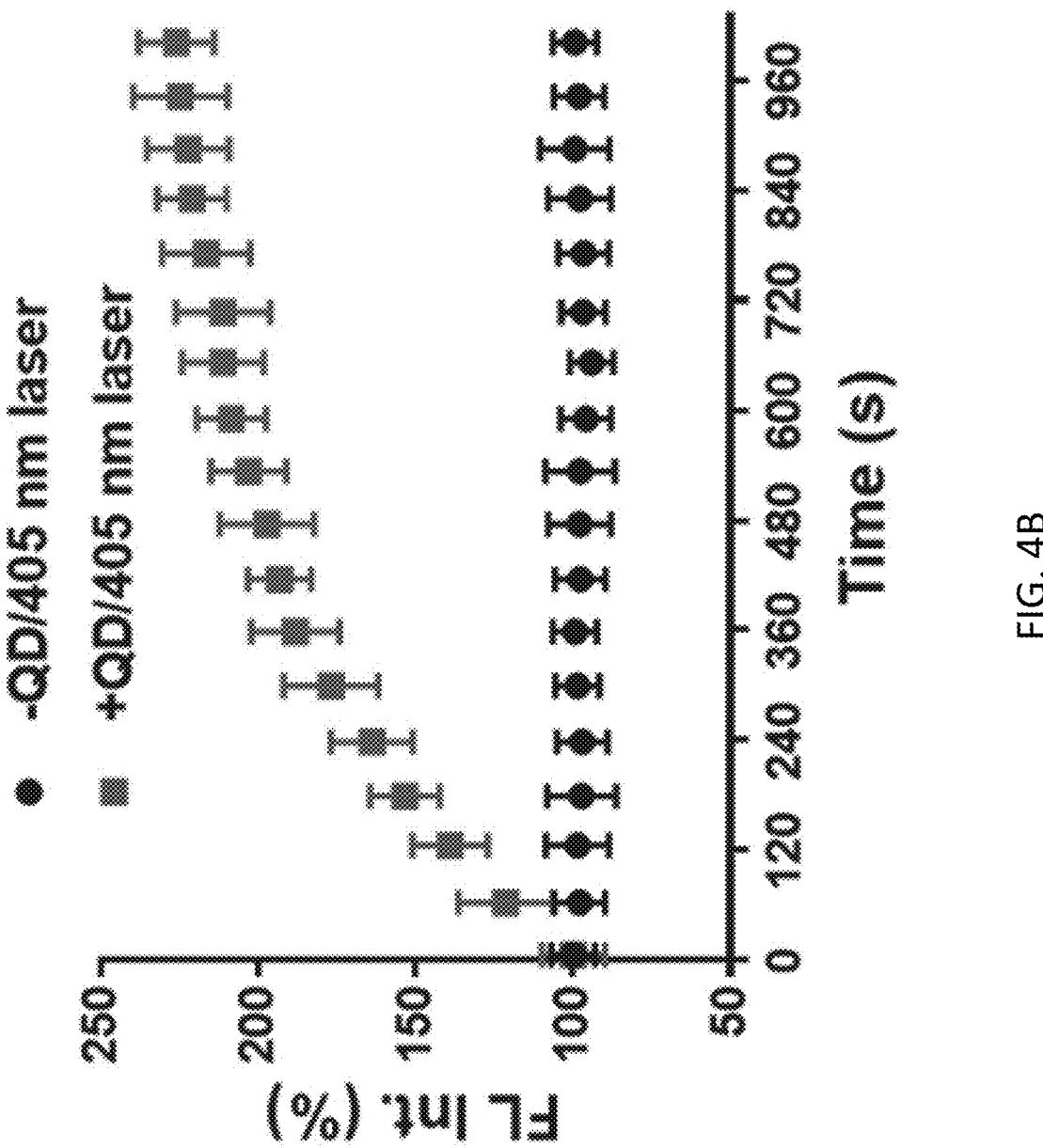

The full functionality and specificity of the FRET system was assessed in cells that were simultaneously expressing His$_6$-ChR-C1V1-iRFP and labeled with 530 nm-emitting QDs (FIG. 4A, left column). Here, excitation of the full ensemble system with the 405 nm laser resulted in the time-resolved increase in membrane depolarization only in those cells labeled with QDs. In non-QD labeled cells, no activation of the ion channel protein was observed upon laser excitation (FIG. 4A, right column). These data are shown graphically in FIG. 4B. Cumulatively, these data demonstrate QD-specificity in the activation of His$_6$-ChR-C1V1-iRFP as well as the quantitative, laser power-dependency of the photoexcitation.

Further Embodiments

This QD-ChR technology could be used in therapeutics for the activation of neurons and muscle cells for non-invasive brain and muscle cell stimulation through the controlled modulation of membrane potential without using optogenetic techniques which requires genetic modification of cells/tissues.

In addition to mediating self-assembly to the ChR protein, the surface of the QD can be used as a scaffold and decorated or conjugated with additional biologicals to facilitate increased targeting to specific cell types. For example, the QD could be decorated with various drugs or therapeutics that can be controllably released by various stimuli (e.g., light, magnetism, ultrasound).

It is expected that the facile, yet specific, self-assembly system described here will find utility in other NP systems that are aimed at the FRET-based, controlled activation of ion channels.

Advantages

Compared to the direct excitation of ChR, the activation of ChR in a FRET configuration using the QD as energy donor as demonstrated here offers a number of distinct advantages. First, the extremely large extinction coefficients of QDs ($\sim10^6$ M$^{-1}$ cm$^{-1}$ at the first exitonic absorption peak) and their absorbance that increases significantly into the UV makes them superior light receivers compared to ChR with ε on the order of $10^5$ M$^{-1}$ cm$^{-1}$. Second, in addition to their extreme brightness, photostability, and long fluorescence lifetime, QDs offer 'tunability' which allows their narrow emission profiles to be matched with the absorption spectra of an increasing number of red-shifted ChRs such as ReaChR, Chrimson, and others whose absorption covers the 590-650 nm window. This can potentially enable the simultaneous combinatorial excitation/activation of multiple ChRs that absorb at discrete wavelength maxima. Further, in the configuration described here, the QD is directly and specifically interfaced with ChR protein and is not simply bound to the plasma membrane using a generic moiety such as cholesterol as has been in other NP-based ion channel activation systems.

This technique eliminates the need for the direct optical excitation of ChR which causes photobleaching, enables the two-photon activation of ChR using the QD as the light-harvesting excitation source, and circumvents the need for genetic transfection/manipulation of cells that is at the heart of 'current state of the art' optogenetics.

Compared to covalent attachment, the polyhistidine-based assembly strategy used here is facile, more tractable, allows ratiometric control of assembly, and does not require cleanup/removal of excess reactants.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Griep, M. H.; Walczak, K. A.; Winder, E. M.; Lueking, D. R.; Friedrich, C. R., Quantum Dot Enhancement of Bacteriorhodopsin-Based Electrodes. Biosens. Bioelectron. 2010, 25, 1493-7.

Griep, M. H.; Winder, E. M.; Lueking, D. R.; Garrett, G. A.; Karna, S. P.; Friedrich, C. R., Förster Resonance Energy Transfer between Core/Shell Quantum Dots and Bacteriorhodopsin. Mol. Biol. Int. 2012, 2012, 910707.

Bouchonville, N.; Le Cigne, A.; Sukhanova, A.; Saab, M.-b.; Troyon, M.; Molinari, M.; Nabiev, I., Controlled FRET efficiency in nano-bio hybrid materials made from semiconductor quantum dots and bacteriorhodopsin. Pro. SPIE 2012, 8460.

Nag, O. K.; Muroski, M. E.; Hastman, D. A.; Almeida, B.; Medintz, I. L.; Huston, A. L.; Delehanty, J. B., Nanoparticle-Mediated Visualization and Control of Cellular Membrane Potential: Strategies, Progress, and Remaining Issues. ACS Nano 2020, 14, 2659-2677.

Carvalho-de-Souza, Joao L.; Treger, Jeremy S.; Dang, B.; Kent, Stephen B. H.; Pepperberg, David R.; Bezanilla, F., Photosensitivity of Neurons Enabled by Cell-Targeted Gold Nanoparticles. Neuron 2015, 86, 207-217.

Carvalho-de-Souza, J. L.; Nag, O. K.; Oh, E.; Huston, A. L.; Vurgaftman, I.; Pepperberg, D. R.; Bezanilla, F.; Delehanty, J. B., Cholesterol Functionalization of Gold Nanoparticles Enhances Photoactivation of Neural Activity. ACS Chem. Neurosci. 2019, 10, 1478-1487.

Muroski, M. E.; Oh, E.; Nag, O. K.; Medintz, I. L.; Efros, A. L.; Huston, A.; Delehanty, J. B., Gold-Nanoparticle-Mediated Depolarization of Membrane Potential Is Dependent on Concentration and Tethering Distance from the Plasma Membrane. Bioconjug. Chem. 2020, 31, 567-576.

What is claimed is:

1. A method of cell depolarization comprising:

providing a cell expressing a channelrhodopsin protein comprising a polyhistidine domain on an extracellular portion thereof;

contacting the cell with a quantum dot configured as a FRET donor to the channelrhodopsin and allowing the quantum dot to self-assemble via metal affinity coordination to the polyhistidine domain; and then stimulating the quantum dot to emit light, thereby optically activating the channelrhodopsin via a FRET process to depolarize the cell.

2. The method of claim 1, wherein said channelrhodopsin protein comprises SEQ ID NO: 1.

3. The method of claim 1, wherein said stimulating comprises two-photon illumination.

4. The method of claim 1, wherein said quantum dot comprises a colloidally stable CdSe/ZnS core/shell.

5. The method of claim 4, wherein said quantum dot comprises a zwitterionic ligand.

6. The method of claim 1, wherein the polyhistidine domain is positioned at an N-terminus of the protein and a far red fluorescent protein (iRFP682) is positioned at a C-terminus of the protein.

* * * * *

SEQUENCE LISTING

```
Sequence total quantity: 1
SEQ ID NO: 1            moltype = AA   length = 751
FEATURE                 Location/Qualifiers
REGION                  1..751
                        note = synthetic construct
source                  1..751
                        mol_type = protein
                        organism = synthetic construct
SEQUENCE: 1
MALLPFQLLA VLFPGGNSHH HHHHGGGSMS RRPWLLALAL AVALAAGSAG ASTGSDATVP   60
VATQDGPDYV FHRAHERMLF QTSYTLENNG SVICIPNNGQ CFCLAWLKSN GTNAEKLAAN  120
ILQWITFALS ALCLMFYGYQ TWKSTCGWET IYVATIEMIK FIIEYFHEFD EPAVIYSSNG  180
NKTVWLRYAT WLLTCPVLLI HLSNLTGLKD DYSKRTMGLL VSDVGCIVWG ATSAMCTGWT  240
KILFFLISLS YGMYTYFHAA KVYIEAFHTV PKGICRELVR VMAWTFFVAW GMFPVLFLLG  300
TEGFGHISPY GSAIGHSILD LIAKNMWGVL GNYLRVKIHE HILLYGDIRK KQKITIAGQE  360
MEVETLVAEE EDAAAKSRIT SEGEYIPLDQ IDINVMAEGS VARQPDLLTC DDEPIHIPGA  420
IQPHGLLLAL AADMTIVAGS DNLPELTGLA IGALIGRSAA DVFDSETHNR LTIALAEPGA  480
AVGAPITVGF TMRKDAGFIG SWHRHDQLIF LELEPPQRDV AEPQAFFRRT NSAIRRLQAA  540
ETLESACAAA AQEVRKITGF DRVMIYRFAS DFSGVVIAED RCAEVESKLG LHYPASAVPA  600
QARRLYTINP VRIIPDINYR PVPVTPDLNP VTGRPIDLSF AILRSVSPCH LEFMRNIGMH  660
GTMSISILRG ERLWGLIVCH HRTPYYVDLD GRQACELVAQ VLAWQIGVME ESEFCRYPAQ  720
WRPLESRGPF EQKLISEEDL NMHTGHHHHH H                                751
```